United States Patent [19]

Aldinger et al.

[11] Patent Number: 4,514,589
[45] Date of Patent: Apr. 30, 1985

[54] ELECTRODE CONNECTING CABLE FOR CARDIAC PACEMAKER

[75] Inventors: Fritz Aldinger, Rodenbach; Albrecht Bischoff, Bruchköbel; Richard Keilberth, Kleinheubach; Franz Sperner, Hanau am Main, all of Fed. Rep. of Germany

[73] Assignee: Heraeus Quarschmelze GmbH, Hanau, Fed. Rep. of Germany

[21] Appl. No.: 412,292

[22] Filed: Aug. 27, 1982

[30] Foreign Application Priority Data

Sep. 3, 1981 [DE] Fed. Rep. of Germany ....... 3134896

[51] Int. Cl.³ .................. H01B 7/04; H01B 5/08; H01B 1/02; A61N 1/04
[52] U.S. Cl. .................. 174/119 R; 174/110 A; 174/126 CP; 128/784
[58] Field of Search .................. 128/784–786, 128/419 P; 174/126 CP, 119 R, 119 C, 110 A

[56] References Cited

U.S. PATENT DOCUMENTS

| | | | |
|---|---|---|---|
| 3,686,428 | 8/1972 | Lombardi et al. | 174/126 CP |
| 3,769,984 | 11/1973 | Muench | 128/419 P |
| 3,837,347 | 9/1974 | Tower | 128/419 P |
| 4,042,753 | 8/1977 | Smith | 174/126 CP |
| 4,273,137 | 6/1981 | Pravoverov et al. | 128/784 |
| 4,287,896 | 9/1981 | Grigorov et al. | 128/784 |

FOREIGN PATENT DOCUMENTS 8004757  2/1981  Netherlands ................ 128/784

*Primary Examiner*—Lee S. Cohen
*Attorney, Agent, or Firm*—Frishauf, Holtz, Goodman & Woodward

[57] ABSTRACT

A cable for connecting a cardiac pacemaker to an electrode inserted in the heart through the blood stream utilizes a die-clad conductor or a number of them, especially several die-clad strands forming a twisted conductor of the stranded type, enclosed in a covering tube of a synthetic elastomer. The core of each die-clad strand is of a highly conducting metal, such as copper or a high-copper alloy. The outer cladding is a metal selected from the group consisting of tantalum, titanium, zirconium, niobium, titanium-base alloys, platinum, platinum-iridium alloys, platinum-palladium alloys and platinum-rhodium alloys. The cladding thickness is in the range from 0.0025 to 0.035 mm, while the cord diameter is between 0.04 to 0.3 mm. When tantalum, titanium, zirconium, niobium or titanium-alloy cladding is used, the outer surface can be made electrically insulating, preferably by anodizing.

10 Claims, 2 Drawing Figures

ELECTRODE CONNECTING CABLE FOR CARDIAC PACEMAKER

This invention concerns a connecting cable for use within the living body between a pacemaker electrode and a cardiac pacemaker unit. Such connecting cables usually have a tubular convering of electrically insulating materials of elastic properties and usually one conductor and sometimes more of them for electric stimulating pulses. The conductor has a core which is of a metal of high electric conductivity and an outer layer of a non-toxic metal, that is corrosion-resistant. A known type of connecting cable of the class above described is disclosed in U.S. Pat. No. 3,749,101. Silicone rubber is utilized for its covering tube. The conductor in the form of a wire within the elastic tube consists of a corrosion resistant alloy containing 20 to 50 percent cobalt, 15 to 30 percent chromium, 5 to 10 percent nickel, up to 18 percent iron, 1 to 10 percent molybdenum, up to 3 percent manganese, up to 0.3 percent carbon and between 0.01 and 0.09 beryllium.

A cable connection for a pacemaker electrode is also known from U.S. Pat. No. 4,273,137. In this case, within a covering tube of silicone rubber an electrical conductor consisting of a multiplicity of electrically conductive fibers is arranged, these fibers having a coating of a corrosion-resistant non-toxic metal alloy such as stainless steel or a cobalt-based alloy. That coating in each case covers a core of a metal of high electrical conductivity. Silver, copper, silver-base alloys or copper-base alloys are used for the core material. The multiplicity of the electrically conducting fibers is enclosed in a shell which again consists of the same corrosion resistant non-toxic metal of which the coating material of the individual fibers consists. Each individual fiber is made of a fine tube serving as the exterior layer which has been filled of a metal of higher electric conductivity.

THE INVENTION

It is an object of the present invention to provide a pacemaker electrode cable in which the electrical losses are reduced to a minimum and one which has good compatibility with living tissue.

Briefly, a die-clad composite conductor is made with a highly conducting core and a cladding layer applied by drawing through a die and consisting of a metal selected from the group consisting of tantalum, titanium, zirconium, niobium, titanium-base alloys, platinum, platinum-iridium alloys, platinum-palladium alloys and platinum-rhodium alloys. The cladding layer thickness lies in the region between 0.0025 and 0.035 mm, while the core diameter is in the range between 0.04 and 0.03 mm.

It has been found particularly useful when the conductor is clad with tantalum, titanium, zirconium, niobium or a titanium-base alloy, to treat the outer surface of the composite conductor to make it electrically insulating, especially by anodizing.

Copper and copper alloys are particularly suitable for the core material of the composite conductor. Pure copper excels in conductivity, but certain alloy additions have been found useful, the most important ones of which are the elements Zr, Ti, Be, Fe, P, Zn and Sn. Examples for such alloys are $Cu0.15Zr$, $Cu4Ti$, $Cu2Be$, $Cu1.7Be$, $Cu0.7Be$, $Cu28Zn$, $Cu37Zn$, $Cu6Sn$, $Cu8Sn$ and $Cu2Fe$.

A core of $Cu0.15Zr$ or of $Cu2Be$, die-clad with tantalum and finally provided with an anodized outer surface has been found particularly useful as the composite conductor for an electrode cable according to the invention. Noble metal can also be used to provide the die-clad composite conductor according to the invention, especially when the noble metal is either a platinum-iridium alloy having up to 40% of iridium and the remainder of platinum, a platinum-palladium alloy with up to 50% palladium, remainder platinum, or a platinum-rhodium alloy with up to 40% rhodium, remainder platinum. The preferred alloys of this type for the clad conductor are $Pt10Ir$, $Pt10Pd$ and $Pt10Rh$. A preferred example for titanium based alloys for cladding conductors into electrode cables in accordance with the invention are the alloys $Ti6A14V$ and $Ti5A12.5Fe$.

The elastic covering tube in which the clad wire is enclosed consists of a synthetic elastomer such as, for example, silicone rubber or flexible polyurethane. It is sufficiently elastic and flexible to make possible its introduction into the heart chamber simply by being carried along through the blood stream.

Electrode cables in accordance with the invention have been subjected to critique test with results showing long service life. Furthermore a long service life for the battery necessary to produce the stimulating pulses is also provided by virture of the high conductivity.

The biocompatability of the clad wire conductor of the cable can be assured by either the noble metal or the other types of metal cladding mentioned above. In the case of the latter, the surface treatment providing insulation, preferably by anodizing, assures that any lesions or other permeabilitys occuring by damage or from other causes can be prevented from providing a false stimulation of the heart.

The die-clad conductors utilized in the present invention have been checked to detect any inter diffusion of the core material and the outer cladding, but nothing of this sort was detected.

THE DRAWING

The invention is further described by way of illustrative example with reference to the annexed drawing, in which;

FIG. 1 shows a perspective view, with the elastic cover partly removed, of an electrode cable according to the invention and FIG. 2 is a cross section, on a larger scale, of the wire used for composite conductors in the electrode cable of FIG. 2.

DESCRIPTION OF THE ILLUSTRATED EMBODIMENT

Figure 1:
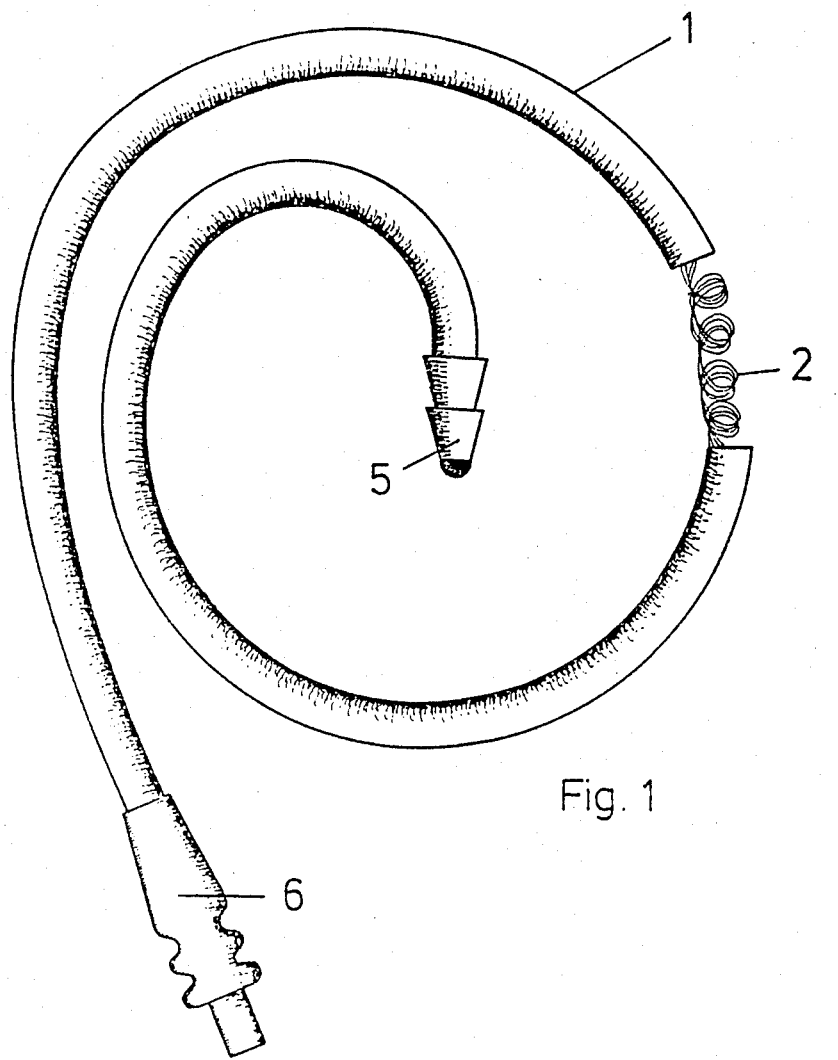

The electrode cable shown in FIG. 1 has a covering tube 1 made of a synthetic elastomer, for example silicone rubber, in which a standard conductor 2 for providing electric stimulation pulses is enclosed. In this illustrated example for individual conductors helically together to make a standard conductor are used, the thickness of the individual conductor strands being 0.11 mm. In the drawing the strands are partly unwound in order to make them individually visible.

The core of a clad wire strand consists of $Cu0.15Zr$ the outer cladding in this case being of externally anodized tantalum. For an electrode cable of this type having a length of 60 cm, a length which corresponds to that normally used for installation of a pacemaker, an electrical resistance of 1.75 ohms was measured. This value is about one order of magnitude smaller than what has been available on the market.

The pacemaker electrode is shown at 5 and at the other end of the cable the plug connector device 6 serves for connection to the pacemaker pulsing unit.

Figure 2:
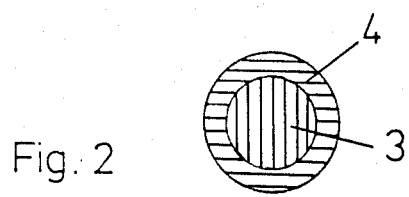

In the schematic cross section shown in FIG. 2 of a clad wire for use in an electrode cable according to the invention, there is shown the core 3 surrounded by the cladding 4. The wall thickness of the cladding in the illustrated case is actually 0.012 mm, while the diameter of the core is 0.086 mm. Usual wall thicknesses for the cladding are in the range from 0.0025 to 0.035 mm and the usual values of the core diameter are in the region from 0.4 to 0.03 mm. Although a single strand conductor could be used, the risks of breakage are reduced and the conductivity is increased without going beyond the above described preferred ranges for core diameter and cladding if a stranded conductor is used. Furthermore a stranded conductor provides increased flexibility, and the degree of flexibility may also depend upon how tightly it is twisted together.

Although the invention has been described with refernce to a particular illustrative example, it would be recognized that modifications and variations are possible with the inventive concept.

We claim:

1. Electrode connecting cable for a cardiac pacemaker having a cover tube of elastic electrically insulating material and at least one conductor strand enclosed therein for electric stimulating pulses, said conductor comprising a core of a metal of high electrical conductivity and a cladding of a corrosion resistant, non-toxic metal, further comprising the improvement, according to the invention, wherein:
   each said conductor strand is a die-drawn clad wire, of which the cladding layer is of a metal selected from the group consisting of tantalum, titanium, zirconium, niobium, titanium-base alloys, platinum, platinum-iridium alloys, platinum-palladium alloys and platinum-rhodium alloys, having a thickness in the range from 0.0025 to 0.035 mm, and
   the core of said conductor is cylindrical when the wire is straight and its diameter is in the range from 0.04 to 0.3 mm.

2. Electrode connecting cable as defined in claim 1 in which said cladding layer is a metal selected from the subgroup consisting of tantalum, titanium, zirconium, niobium and titanium-base alloys, and in which the outer surface of said cladding layer is electrically insulating as the result of insulation-forming treatment.

3. Electrode connecting cable as defined in claim 1 or claim 2 in which said conductor core is of a metal selected from the group consisting of copper and alloys of copper.

4. Electrode connecting cable as defined in claim 3 in which said conductor core is an alloy of copper and at least one chemical element selected from the group consisting of Sn, Ti, Be, Fe, P, Zn and Sn.

5. Electrode connecting cable as defined in claim 3 in which said conductor core is a copper alloy selected from the group consisting of Cu0.15Zr; Cu4Ti; Cu2Be; Cu1.7Be; Cu28Zn; Cu37Zn; Cu6Sn; Cu8Sn; and Cu2Fe.

6. Electrode connecting cable as defined in claim 2 in which said conductor core consists of a metal selected from the group consisting of Cu0.15Zr and Cu2Be and said conductor cladding consists of tantalum and has its outer surface anodized.

7. Electrode connecting cable as defined in claim 1 in which said cladding material consists of a platinum alloy selected from the group consisting of platinum iridium alloys containing not more than 40% iridium, platinum-rhodium alloys containing not more than 40% rhodium and platinum-palladium alloys containing not more than 50% palladium, the remaining percentage of the alloy composition being in each case sustantially all platinum.

8. Electrode connecting cable as defined in claim 7 in which said conductor core is a metal selected from the group consisting of copper and copper alloys and said cladding material is a platinum alloy selected from the group consisting of Pt10Ir, Pt10Pd and Pt10Rh.

9. Electrode connecting cable as defined in claim 8 in which said conductor core consists of a copper alloy selected from the group which consists of Cu0.15Zr and Cu2Be.

10. Electrode connecting cable as defined in claim 1, 2, 6, 7, 8 or 9, in which a plurality of said conductor strands are enclosed in said cover tube and said conductor strands are twisted together inside said cover tube to form a stranded composite conductor.

* * * * *